United States Patent [19]

Johnson et al.

[11] Patent Number: 4,939,466
[45] Date of Patent: Jul. 3, 1990

[54] METHOD AND APPARATUS FOR SENSING THE REGENERATION OF A DIESEL ENGINE PARTICULATE TRAP

[75] Inventors: John H. Johnson, Houghton, Mich.; Peter V. Woon, Columbus, Ind.

[73] Assignee: Board of Control of Michigan Technological University, Houghton, Mich.

[21] Appl. No.: 336,201

[22] Filed: Apr. 10, 1989

[51] Int. Cl.⁵ ............................................. G01N 27/62
[52] U.S. Cl. .................................... 324/464; 324/466; 324/701; 324/717; 324/727; 73/861.09
[58] Field of Search ........... 73/861.09, 861.08, 861.05; 324/65 P, 65 R, 61 P, 464, 466, 465, 701, 717, 724

[56] References Cited

U.S. PATENT DOCUMENTS

| | | | |
|---|---|---|---|
| 3,679,973 | 7/1972 | Smith | 324/464 |
| 4,127,029 | 11/1978 | Murtin | 73/861.09 |
| 4,456,883 | 6/1984 | Bullis et al. | 324/464 |
| 4,584,531 | 4/1986 | Couch | 324/464 |
| 4,628,267 | 12/1986 | Lee | 324/65 R |
| 4,644,263 | 2/1987 | Johnson | 324/65 P |

FOREIGN PATENT DOCUMENTS

| | | | |
|---|---|---|---|
| 2410365 | 9/1975 | Fed. Rep. of Germany | 73/861.09 |
| 2296840 | 7/1976 | France | 73/861.09 |
| 0870943 | 10/1981 | U.S.S.R. | 73/861.09 |

Primary Examiner—Reinhard J. Eisenzopf
Assistant Examiner—Jose M. Solis
Attorney, Agent, or Firm—Michael, Best & Friedrich

[57] ABSTRACT

A diesel engine exhaust system is provided with a particulate trap for collecting the products of incomplete combustion during the engine power cycle. A sensing mechanism including an electrode downstream of the trap and a signal generating circuit provides a positive indication of occurrence of regeneration of the trap. Charged particles generated during regeneration induce a charge of the electrode, that charge activates the signal generating circuit and it, in turn, produces an indication external of the exhaust system that trap regeneration is occurring. That indication can be in the operator's compartment.

19 Claims, 1 Drawing Sheet

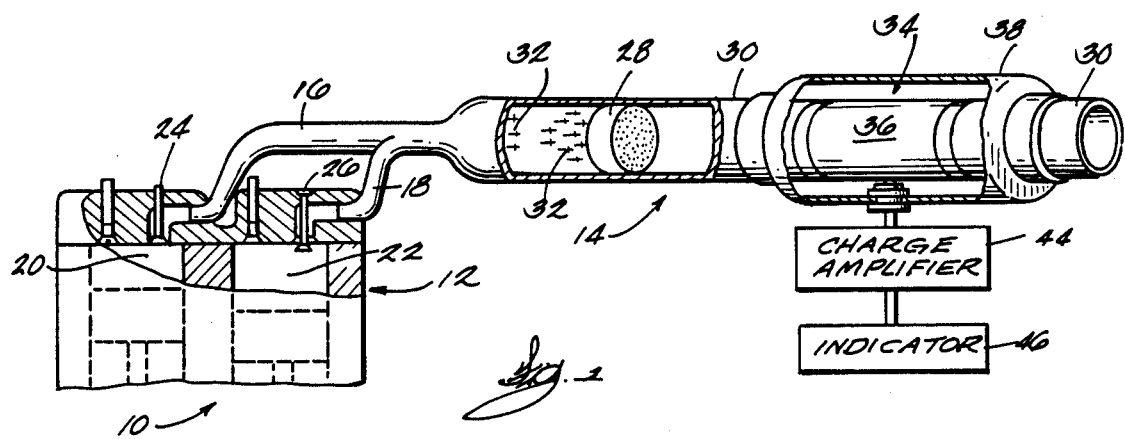
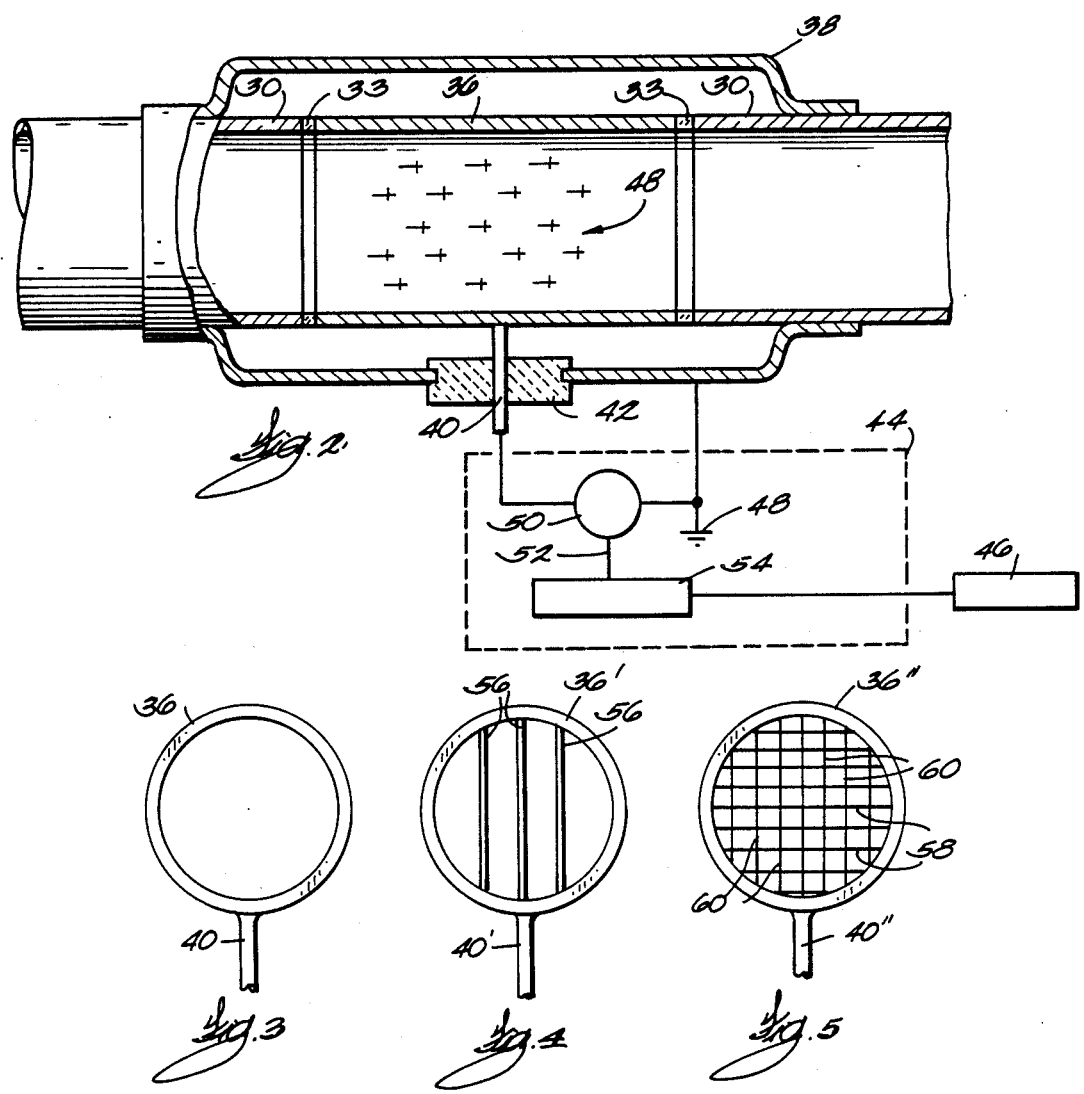

METHOD AND APPARATUS FOR SENSING THE REGENERATION OF A DIESEL ENGINE PARTICULATE TRAP

BACKGROUND OF THE INVENTION

This invention relates to internal combustion engines and, more particularly, to diesel engines including particulate traps in the exhaust system. Still more particularly, this invention relates to methods and apparatus for sensing the regeneration of such particulate traps.

In internal combustion engines such as diesel engines, various particles are present in the exhaust gases as a result of incomplete combustion. It is not desirable to discharge these particles into the atmosphere and a known method of preventing such undesirable discharge is to provide the exhaust system of the engine with a particulate trap, or filter, which intercepts and collects the particles.

It is also well know that, from time to time, the particulate trap should be regenerated and this can be done using one of several well known procedures. In the regeneration process, the entrapped particles are burned off the trap and the products of that combustion are allowed to pass through the exhaust system to the atmosphere. Although the products of regeneration are further broken down from what results in the power combustion cycle, this can still generate pollutants. For that reason, it is desirable for the regeneration control system, and possibly the operator of the vehicle, to know when regeneration of the particulate trap is occurring, i.e., beginning and ending. A known type of regeneration sensor measures the pressure differential across the particulate trap, but such sensors are expensive and are not very accurate.

SUMMARY OF THE INVENTION

This invention provides a method and apparatus for sensing the regeneration of a particulate trap. During normal operation of a diesel engine equipped with a particulate trap, the trap intercepts the bulk of the products of incomplete combustion. It has been observed that particles produced during regeneration and which pass through the exhaust system downstream of the trap, are electrically charged, typically positively charged.

In accordance with this invention, a particulate trap is located in the exhaust passage and an electrode is positioned downstream of the particulate trap in the exhaust passage. The electrode is capable of detecting the presence of charged particulates flowing through the exhaust passage. Preferably, the electrode is annular, has an inner diameter substantially equal to the inner diameter of the exhaust passage, and is coaxial with the exhaust passage. According to known principles, the charged particles passing through the annular electrode will induce a current in the electrode. In the preferred embodiment of the invention, a charge amplifier is connected to the electrode and provides an output voltage proportional to the integral over time of the current induced in the electrode. The integral of the current is indicative of the net charge on the particles passing through the electrode. The generated output voltage is used to provide a signal for the operator of the vehicle that regeneration of the trap is in process.

Furthermore, and in the preferred embodiment, the electrode has a length (in the direction axially of the exhaust passage) equal to between two and three times the inner diameter of the exhaust passage. Increasing the length of the electrode increases its sensitivity because the number of charged particles contained within the electrode at any given time is increased, thereby increasing the net electric field "seen" at the electrode surface. Additionally or alternatively, the electrode can be provided with a grid extending across the exhaust passage. The grid is electrically connected to the electrode and this increases the sensitivity of the electrode because it decreases the distance between more of the charged particles and the sensing surface, i.e., the electrode and the grid.

Other features and advantages of the invention will become apparent to those skilled in the art upon review of the following detailed description, claims and drawings.

DESCRIPTION OF THE DRAWINGS

FIG. 1 is a diagrammatic view of a portion of an internal combustion engine illustrating a pair of cylinders and an exhaust passage including a particulate trap and a sensor.

FIG. 2 is an enlarged, partial, sectional view of the exhaust passage, sensor, and signal generating circuit.

FIG. 3 is an end view of the sensor.

FIG. 4 is an end view of an alternative sensor construction.

FIG. 5 is an end view of yet another alternative sensor construction.

Before one embodiment of the invention is explained in detail, it is to be understood that this invention is not limited in its application to the details of construction and/or the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF PREFERRED EMBODIMENT

FIG. 1 illustrates, in part, a pair of cylinders 10 and 12 of a diesel engine. The cylinders are connected to an exhaust system 14 through exhaust passages 16 and 18 which, in turn, communicate with the interior combustion chambers 20 and 22 through exhaust valves 24 and 26. The diesel engine cylinders are of conventional construction and the combustion and exhaust cycles of the cylinders are conventional and will not be described in detail in this application.

It is well known that during the operation of a diesel engine periodic combustion in each cylinder and subsequent periodic exhaust of the products of combustion through the exhaust valves flows through the exhaust system in what can be viewed as relatively distinct groups of exhaust gases. It is also well known that because of ionization which occurs during the combustion process, the individual particles making up the particle groups are electrically charged. It is also relatively well known that these products of combustion in a diesel engine are undesirable pollutants and are not desirable for exhaust directly into the atmosphere. To prevent discharge of raw exhaust gases, this invention proposes to insert a trap, or filter, in the exhaust package. In FIG. 1, this trap 28 is illustrated as being positioned in a generally cylindrical section 30 of the exhaust system. The groups of exhaust particles 32 are intercepted in the exhaust system by the trap 28 and collected on the trap.

It is also proposed to periodically regenerate the trap 28 by, in effect, burning the trapped particles 32 off of the trap 28. Those particles, during the burning process, may blow through the pores of the trap, or be burned forming other particles (soot) freed from the trap and carried through the exhaust system 14. There are several well known ways of initiating and maintaining the regeneration process, any one of which may be used in connection with this invention and will not be described in this application.

The products of the regeneration process, although cleaner than the products of the basic combustion process in cylinders 10 and 12 because of further combustion of the particles 32, the mixture of gas and particulates issuing from trap 28 are still pollutants and the control system or vehicle operator should know when the regeneration process is occurring so that the system/operator can conduct itself accordingly. This invention is concerned with the detection of the regeneration process and providing a positive indication to the system/operator that it is occurring.

More specifically, an electrode assembly 34 is positioned in the exhaust system 14 downstream of trap 28. The electrode assembly is made up of a cylindrical electrode 36 which is positioned in the exhaust system coaxially with the longitudinal axis of the exhaust system. The electrode 36 is annular in cross section as can be seen in FIG. 3 and its inner diameter is substantially equal to the inner diameter of the exhaust pipe 30. This insures that substantially all of the products of combustion of the regeneration process will flow through the interior of the electrode 36.

As illustrated in FIG. 2, the electrode 36 is connected into exhaust pipe 30 and may actually form a portion thereof but is electrically isolated from the exhaust pipe 30 by insulator rings 33. Electrode 36 is then coaxial with and may actually form a portion of the exhaust pipe 30. The electrode 36 and its connection in exhaust pipe 30 is shielded by a metallic cover 38.

An electrically conductive stem, or terminal, 40 is connected to electrode 36 which extends through a support block 42 constructed of electrical insulating material. Stem 40 communicates with a charge amplifier 44 which in turn is connected to a suitable indicator 46. In this manner, and as will be described more specifically hereinafter, as the charged particles flow from trap 28 through electrode 36, a signal will be generated, amplified and integrated in the charge amplifier 44 and transmitted to the indicator 46 to advise the operator or control system that the regeneration process is occurring.

As was referred to previously, the products of combustion during the regeneration process, which are illustrated schematically as particles 48 in FIG. 2, are electrically charged, the charge of these particles is believed to be predominantly positive and, therefore, the particles are so illustrated in a schematic manner in FIG. 2. The electrical field associated with these charged particles as they pass through the electrode 36, cause a charge of opposite polarity to build up on the surface of the electrode in accordance with a well known phenomena, Gauss' Law.

With reference to FIG. 2 in the electrical schematic of charge amplifier 44, electrode 40 is connected to ground 48 through a current sensing circuit 50 which provides a signal determined by the integral of the current from electrode 36 to ground as a result of the induced charge from particles 48. That signal is transferred through connector 52 to a voltage output circuit 54 which in turn produces a control signal to indicator 46. The elements of the charge amplifier circuit and their arrangement are conventional and, therefore, are not described in detail, however, the charge amplifier is capable of providing an output voltage from circuit 54 which is proportional to the integral over time of the current into the amplifier through terminal 40 as a result of the induced charge.

Gauss' law states that the ratio of the charge seen by the electrode 36 is proportional to the fraction of the electrical field lines of the charged particles which contact or otherwise influence the surface of electrode 36. With that observation, it was determined that the length of the electrode 36 should be a consideration in determining the sensitivity of the electrode at any given time. By increasing the length of the electrode the net electrical field "seen" by the electrode surface can be increased. Preferably, the axial length of the electrode 36 should be at least two times the diameter of the electrode and/or the exhaust pipe 30, or approximately two to three times that diameter.

Another arrangement for increasing the electrode sensitivity is illustrated in FIG. 4. In this illustration, the sensor 36' is provided with a series of metallic plates 56 which have their elongated, planar surfaces running parallel to the axis of the electrode and arranged in parallel fashion in the electrode 36'. The axial length of these plates is generally equal to the axial length of the electrode. If the electrode is an annulus, then these "plates" will be more in the nature of wires or rods. In FIG. 5, a sensor 36" carries a grid made up of a series of horizontal wires 58 cross by a series of vertical wires 60. With either of these arrangements, a decrease in distance between more of the charged particles and the actual sensing surface occurs, the plates 56 and wires 58 and 60 being electrically connected to electrode 36' thereby forming an extension thereof. This has the effect of increasing the output from the sensor ring, current to amplifier 44, as the amount of sensing surface exposed to the charged particles has been increased.

To illustrate the effectiveness of the electrode sensor in detecting the occurrence of regeneration cycle, a test utilizing the configuration illustrated in FIGS. 1 and 2 was performed utilizing a caterpillar 3208 engine and an electrode configuration as illustrated in FIG. 4. The engine was operated at rated speed [approximately 2800 rpm and at 28% of load (approximately 98 ft-lbf)] during which the particulate trap became loaded with soot (the products of incomplete combustion on the power cycle), loading of the trap was produced in approximately 40 minutes. The charge amplifier and the output signal in that amplifier was connected to a strip chart recorder. No charge was detected by the electrode sensor during this loading period. The particulate traps were then regenerated with the engine operating at intermediate speed (approximately 1680 rpm and at full load, 472 ft-lbf). The strip chart indicated a marked, peaked output after initiation of the regeneration cycle and, similarly, the strip chart indicated a marked fall off, a no output signal condition at the termination of the regeneration cycle.

Then, in accordance with this invention, during normal operation of the diesel engine, the charged particles resulting from incomplete combustion in the combustion chambers collect on the particulate trap and no signal is provided by the electrode 36 in the amplifier 44. The exhaust gases passing through the electrode while the particulate trap is loading contain few, if any, charged particles, and little or no current is induced in the electrode and the output voltage of the charge amplifier to the indicator is nonexistent. It should be recognized that there is the possibility for some of the charged particles incomplete combustion to leak through the traps, but it has been observed that these are not sufficient to activate the electrode or the charge amplifier. During the regeneration cycle, the particles accumulated on the particulate trap are burned off and take on a positive electric charge and pass through the exhaust passage downstream to the electrode where the charge on those particles is sensed. The charged particles induce a current from the electrode into the charge amplifier which then provides an output voltage proportional to the integral over time of the current in the electrode, i.e., proportional to the total charge of the particulates passing through the electrodes and sensed by the electrode. This then provides a signal at the indicator 46, which can be positioned in the operator's compartment giving him a clear indication that the regeneration process is occurring so that he can maneuver the vehicle accordingly. After the regeneration cycle is completed, the number of charged particles passing through the electrode 36 diminishes to a point where sufficient current is no longer induced in the electrode 36, e.g., it is near zero, the indicator is turned off and the operator now knows that the regeneration cycle has terminated.

This invention has been discussed in terms of the output of sensor being a signal to or at the indicator 46. That indicator could be a light or the like inside the operator compartment for the purpose of signaling to the operator that the regeneration cycle is taking place. In addition, the signal could be used to power a recording system to preserve a record of the regeneration event. Beyond that, the signal could be used to activate controls which could either adjust the combustion cycle or feed back to the regeneration cycle.

Although this invention has been illustrated and described in connection with several embodiments thereof, it will be apparent to those skilled in the art that various changes and modifications may be made therein without departing from the spirit of the invention or from the scope of the appended claims.

Various features of this invention are set forth in the following claims.

We claim:

1. In combination in an internal combustion engine having a combustion chamber,
    an exhaust passage communicating with said combustion chamber,
    a particulate trap located in said exhaust passage,
    charge sensing means located downstream of said particulate trap in said exhaust passage for detecting the presence of electrically charged particulates passage through said exhaust passage,
    said charge sensing means including electrode means generally cylindrical in configuration and having the axis thereof extending in the direction of flow through said exhaust passage, and
    charge amplifying means electrically connected to said sensing means and accepting electrical current from said sensing means and producing an electrical signal indicative of said electrically charged particles flowing through said sensing means.

2. The combination as set forth in claim 1 wherein said charge sensing means includes electrode means exposed to the interior of said exhaust passage and inductively responsive to charged particulates passing said electrode means, and said charge amplifying means provides an output proportional to the integral over time of the current induced in said electrode means.

3. An apparatus as set forth in claim 2 and further comprising generally cylindrical duct means defining at least a portion of said exhaust passage and having an inner diameter, and wherein said electrode means is generally cylindrical having an inner diameter equal to said inner diameter of duct means and a length extending axially of said exhaust passage, said length being at least two times said inner diameter.

4. An apparatus as set forth in claim 3 wherein said electrode means is substantially coaxial with said exhaust passage.

5. An apparatus as set forth in claim 4 and further comprising electrically conductive grid means supported across and in electrical contact with said electrode means.

6. An apparatus as set forth in claim 5 further comprising indicating means connected with and responding to the output of said charge amplifying means to provide an indication external of said exhaust system of the presence of charged particulates at said electrode means.

7. A sensor for detecting the presence of charged particulates in the exhaust passage of an internal combustion engine, said sensor comprising
    electrode means connected in said exhaust passage with the inner surface thereof exposed to and electrostatically responsive to charged particulates passing through said exhaust passage and past said electrode means, said electrode means being generally cylindrical and the inner surface thereof having an extension along the path of exhaust through said passage and
    means connected to said electrode means and responsive to the current in said electrode means for indicating the passage of charged particulate through said electrode means.

8. An apparatus as set forth in claim 7 wherein said indicating means provides an output proportional to the integral over time of the current flowing through said electrode means.

9. An apparatus as set forth in claim 8 wherein said exhaust passage has an inner diameter, and wherein said electrode means has an inner diameter approximately equal to the inner diameter of said exhaust passage and a length axially of the exhaust passage, said length being at least two times the diameter of the exhaust passage.

10. An apparatus as set forth in claim 9 wherein said electrode means further includes electrically conductive grid means supported across and electrically connected in said electrode means.

11. An apparatus as set forth in claim 10 further comprising indicating means connected with and responding to the output of said charge amplifying means to provide an indication external of said exhaust system of the presence of charged particulates at said electrode means.

12. An apparatus as set forth in claim 9 wherein said charge amplifying means provides an output proportional to the integral over time of the current flowing between said electrode means and ground.

13. A method for detecting the regeneration of a particulate trap in the exhaust passage of an internal combustion engine, said method comprising the steps of
 inducing an electrode charge onto electrode means at a point downstream of said trap and from charged particulates produced by the regeneration process as they flow past said electrode means,
 generating an electrical signal proportional to said charge, and
 converting said electrical signal to another signal external of said exhaust passage indicative of the presence of said charged particulates at said electrode.

14. The method as set forth in claim 13 wherein said electrical signal is proportional to the integral over time of the current produced by the charge induced in said electrode means.

15. In combination with a diesel engine having combustion chambers, an exhaust system connected to said combustion chambers, and a trap located in said exhaust system for interrupting particulates resulting from incomplete combustion and wherein said trap is periodically regenerated by burning those particulates off of the trap, the improvement comprising, in combination,
 an electrode connected in said exhaust system, downstream of said trap in said exhaust system, said electrode having an inner surface exposed to the flow through said exhaust system and having a configuration generally corresponding to the inner configuration of the exhaust system to which it is connected so that substantially all of the exhaust flowing through said exhaust system flows through said electrode and the electrical charge on said particulates induces a charge on said electrode,
 charge amplifier means electrically connected to said electrode and receiving current therefrom as a result of said induced charge, said charge amplifier means generating a signal proportional to said induced charge and said current, and
 indicating means connected to said charge amplifier means and receiving said signal therefrom, said indicating means being located external of said exhaust system and providing an indicator that a charge is being induced in said electrode and said regeneration is in process.

16. The combination of claim 15 wherein said exhaust system is further characterized in having a generally cylindrical section and wherein
 said electrode is connected in said generally cylindrical section and is generally cylindrical having an inner diameter at least equal to the inner diameter of said cylindrical exhaust system section.

17. The combination of claim 15 wherein said electrode is coaxial with said exhaust system cylindrical section and has a length in the range of at least two times said inner diameter.

18. The combination of claim 17 wherein said electrode length is in the range of two to three times said inner diameter.

19. The combination of claim 17 wherein said electrode further includes planar plates extending in relatively parallel relationship in said electrode with the planar surfaces thereof extending generally parallel to the longitudinal axis of said exhaust system section and said electrode, said plates being electrically connected to said electrode and having a length in the axial direction of said electrode generally equal to said electrode axial length.

* * * * *